United States Patent [19]

Cole et al.

[11] Patent Number: 4,934,375

[45] Date of Patent: Jun. 19, 1990

[54] FLUSH-VALVE ASSEMBLY FOR BLOOD PRESSURE MEASUREMENT CATHETER

[75] Inventors: James E. Cole; Maurice A. Warren, both of Ventura; Douglas R. Savage, Oxnard, all of Calif.

[73] Assignee: Spectramed, Inc., Oxnard, Calif.

[21] Appl. No.: 394,253

[22] Filed: Aug. 7, 1989

Related U.S. Application Data

[63] Continuation of Ser. No. 296,287, Jan. 11, 1989, abandoned, which is a continuation of Ser. No. 164,238, Mar. 4, 1988, abandoned.

[51] Int. Cl.[5] .............................................. A61B 5/02
[52] U.S. Cl. .................................... 128/673; 128/748; 604/246; 251/334
[58] Field of Search ............................... 128/672–675, 128/748; 604/30, 32–34, 246–249, 236–238, 256; 251/61.1, 331–334, 335.1–335.3, 117–118, 309, 209; 137/238, 510

[56] References Cited

U.S. PATENT DOCUMENTS

| | | | |
|---|---|---|---|
| 3,675,891 | 7/1972 | Reynolds et al. | 128/673 X |
| 4,192,303 | 3/1980 | Young et al. | 604/250 |
| 4,278,083 | 7/1981 | Young et al. | 604/250 |
| 4,291,702 | 9/1981 | Cole et al. | 128/675 |
| 4,337,770 | 7/1982 | Young et al. | 604/30 |
| 4,431,009 | 2/1984 | Marino, Jr. et al. | 128/673 |
| 4,444,198 | 4/1984 | Petre | 128/673 |
| 4,456,223 | 6/1984 | Ebling | 604/33 X |
| 4,501,300 | 2/1985 | Murphy | 604/246 X |
| 4,517,844 | 5/1985 | Powell | 128/672 X |
| 4,537,387 | 8/1985 | Danby et al. | 604/249 X |
| 4,545,389 | 10/1985 | Schaberg et al. | 128/675 X |
| 4,624,662 | 11/1986 | Le | 128/675 X |
| 4,645,496 | 2/1987 | Oscarsson | 128/673 X |
| 4,696,305 | 9/1987 | Von Berg | 128/673 |
| 4,703,759 | 11/1987 | Merrick et al. | 128/673 |
| 4,739,770 | 4/1988 | Stephens et al. | 128/675 |

FOREIGN PATENT DOCUMENTS 3207044 10/1983 Fed. Rep. of Germany ...... 128/673

Primary Examiner—Angela D. Sykes
Attorney, Agent, or Firm—Roger M. Rathbun; Larry R. Cassett

[57] ABSTRACT

A resilient valve core, biased against its seat in a molded body, controls large flow volumes for flushing. A small resilient tube embedded in the core bypasses the valve to provide smaller flow volumes for IV-fluid drip. For flushing, the core is deformed, rather than bodily moved, relative to the body. A fluid-flow channel is recessed along one side of the valve cavity, and the valve seat forms a short barrier across this channel. The core is a T-shaped unitary member; the center of the "upper" surface of the T crossbar is biased against the seat, and the extrema of the crossbar are hermetically sealed against the valve body, while the stem of the T extends outward from the body. A user squeezes a cowling mounted outside the body to start and control flushing. The cowling itself deforms to pull the stem of the T outward, deforming the T and separating the middle of its crossbar portion from the valve seat. A user can elect to grasp and pull the stem directly. Parts of the upper side of the extrema of the T crossbar are relieved, forming a smooth fluid-flow transition with the inlet and outlet. These paths, the relieved parts of the crossbar, and the cavity interior are all smooth, gently tapering and well fitted, forming nearly an in-line flush path to minimize gas-bubble trapping.

30 Claims, 5 Drawing Sheets

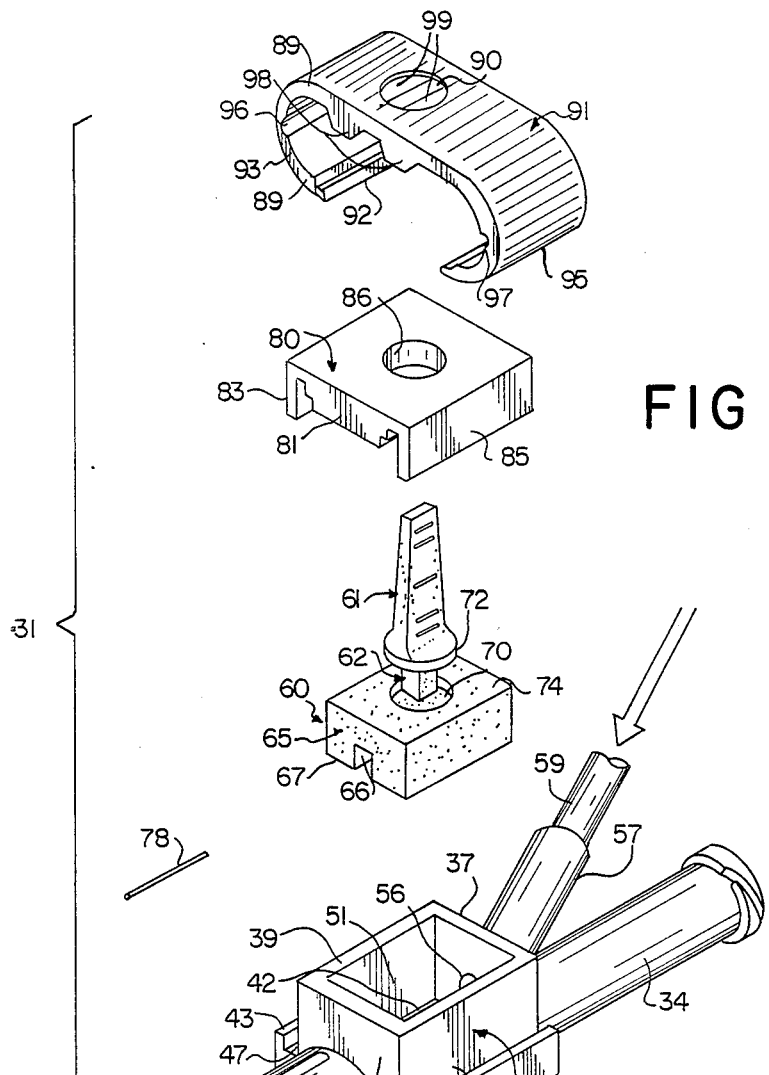
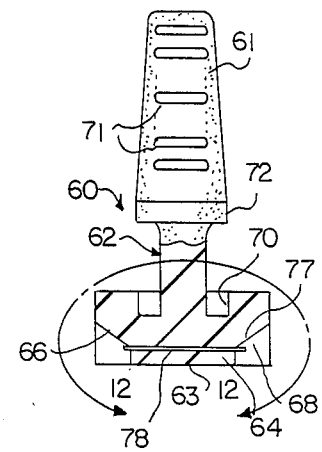
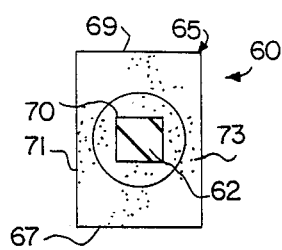
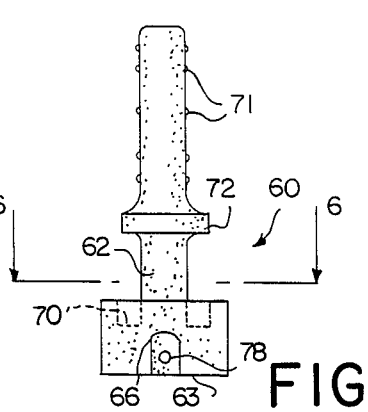
FIG. 3
FIG. 4
FIG. 5
FIG. 6

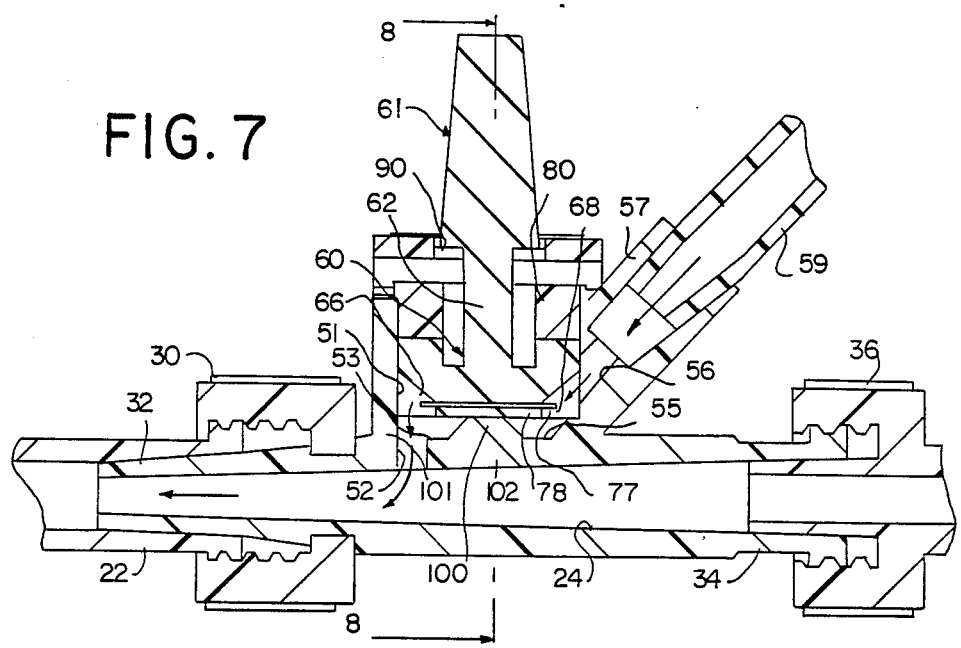
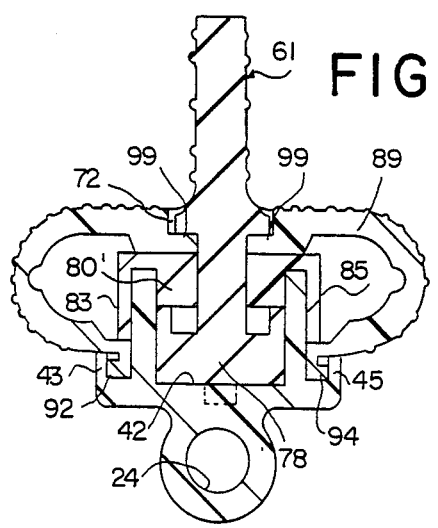
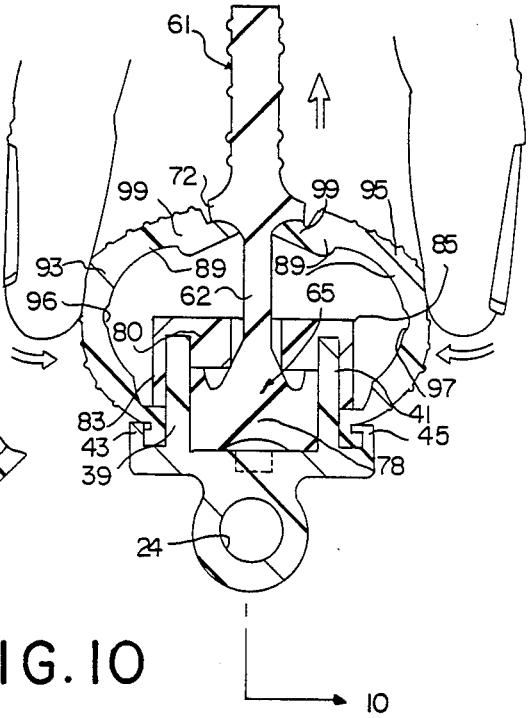
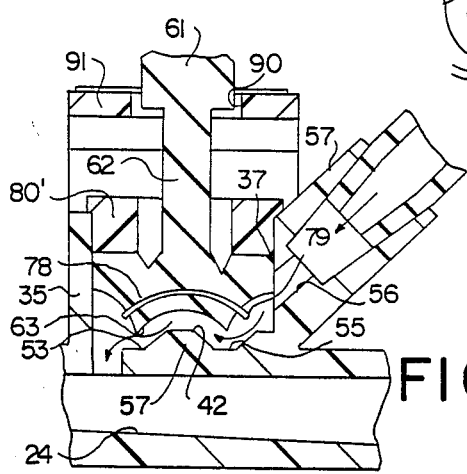

FLUSH-VALVE ASSEMBLY FOR BLOOD PRESSURE MEASUREMENT CATHETER

This is a continuation of application Ser. No. 296,287, filed Jan. 11, 1989, now abandoned, which was a continuation of application Ser. No. 164,238, filed Mar. 4, 1988, now abandoned.

BACKGROUND

1. Field of the Invention

This invention relates generally to appliances for medical use; and more particularly to a flush-valve assembly for a blood-pressure measurement catheter.

2. Prior Art

It is well known in the art of invasive blood-pressure measurement to determine a patient's blood pressure by monitoring the pressure in a liquid column that is in communication with the patient's blood stream. Thus in some cases a cannula is implanted in the patient's body, with its tip in a blood vessel. Typically a tube or "line" connects the cannula to an elevated supply container of saline solution or liquid used in medicating the patient. A blood-pressure measurement device is installed partway along the tube between the cannula and the supply.

In other cases, essentially the same system can be used with a special-purpose catheter that is implanted in a patient for other purposes. In particular, a cardiovascular catheter used for diagnosis or therapeutic purposes, or both, may have a lumen reserved for pressure measurement and/or administration of medication.

A slow flow, nominally three centimeters per hour, or as we will say herein a "drip-rate flow," of liquid into the patient's body is maintained to keep the cannula and supply line open, and to verify that it is open. Sometimes a small amount of anticoagulation compound, such as heparin, is added to the liquid.

Also within the range of "drip-rate flow," for neonatal, pediatric and some other special applications, are values such as thirty cubic centimeters per hour. In such applications administration of lipids or certain other medications sometimes requires larger orifices.

In starting and maintaining the operation of such a system, medical personnel must flush the blood-pressure measurement device and the line—to fill them, and to eliminate bubbles of air or any other gas. As is well known, removal of gas bubbles is important both for measurement accuracy and for patient safety.

By virtue of their compressibility, bubbles can support an unknown pressure differential between the measurement site and the patient's blood stream, directly constituting an error in the measurement. In addition, if bubbles are allowed to enter the patient's blood vessel serious injury to the patient can result.

Accordingly special flush-valve assemblies have been introduced to facilitate such flushing of the line and the measurement device, and to establish a suitable drip-rate flow after flushing is complete. U.S. Pat. No. 4,291,702, which issued Sept. 29, 1981, to Cole and Thornton, is representative of the state of the art in flush-valve assemblies for pressure-measuring catheters.

The Cole and Thornton device has a lever-actuated plunger that lifts an O-ring seal away from a seat to open the valve. When the valve is open it allows relatively high fluid volumes—or as we will here say in shorthand form, a "flush-rate flow"—of liquid to pass from the supply container through the pressure-measurement device to the blood-pressure measurement catheter. Usually flush-rate flows are manually variable, and typically perhaps two or three orders of magnitude higher than drip-rate flows.

The Cole and Thornton valve assembly also has a fine lumen or tube passing through the valve core, so that controlled drip-rate volumes of liquid can trickle from the intravenous-liquid or like supply into the catheter even when the lever is not actuated. Other patents, such as Schaberg and Cole U.S. Pat. No. 4,545,389, teach incorporation of a pressure-measurement sensor into a unitary assembly with the valve.

Such devices have been found extremely useful in medical applications and in fact enjoy wide commercial success Yet in some respects they bear improvement.

In particular, known valve assemblies are relatively costly. This is a particularly important limitation, since for many medical applications involving patients who may be carrying extremely dangerous and highly contagious disease, it is desirable to treat the flush-valve assemblies as disposable.

Furthermore, known valve assemblies have several regions where eddies tend to form in fluid flow, and also have some narrow niches or crevices between some components. Both these phenomena tend to trap gas bubbles in positions where they cannot be readily flushed out of valves during the routine preliminary flushing described above.

As already mentioned, bubbles can degrade measurement accuracy or even injure the patient. Generally a skilled user can remove all the bubbles, but only with difficulty and at the cost of some time.

Some commercially available devices have a thick-walled glass capillary tube that passes through an elastomeric tube. Drip-rate flow passes through the interior of the capillary.

On the outside of the capillary at about its midpoint is a circumferential boss or radial flange that stands the elastomeric tube away from the rest of the glass tube. To institute flush-rate flow, a user squeezes the outside of the device to deform the elastomeric tube.

In this deformation the elastomer is pulled away from the outside of the capillary, allowing fluid to flow through the resulting space. Such devices are described, in particular, by Young et al U.S. Pat. Nos. 4,192,303, 4,278,083, and 4,337,770.

These devices are useful but do have some drawbacks. In particular, it has been noticed that in some blood-pressure monitoring systems employing such valves there appear to be spurious oscillations in the blood-pressure readouts. These spurious oscillations interfere with the accurate and reliable measurement of actual variations in blood pressure.

Similar interferences have also been noted in some devices—e.g., the Cole-Thornton type—that use a spring-biased lever for flush control. In both cases, the interfering oscillations have been traced to mechanical resonances in the valves. Such resonances are sometimes within the effective frequency range of blood-pressure variations of interest, namely ten to fifteen hertz and below. Therefore these resonances mask or interfere with detection of these important variations in blood pressure.

The inventors of the squeeze-type valve, Young et al., in effect concede the presence of such problems in their earlier devices by including additional compensating structure in their two later continuation-in-part applications. In particular, they include within their resilient outer tube a rigid cylinder that radially constrains the downstream end of the resilient tube and to a large extent isolates it from the fluid column. In combination with other structural features, the rigid cylinder also constrains the inner thick-walled glass capillary tube both radially and axially.

Young et al. explain that the cylindrical extension and other constraining structures have "a beneficial effect on the wave forms and other clinical data produced by the monitoring apparatus." They do not, however, specifically teach either the problem cured by this "beneficial effect" or indeed what the effect itself is—even though it is apparently the subject of a continuation-in-part application and a divisional therefrom.

It seems likely that the "beneficial effect" is some reduction in resonant interferences. Even the newer configuration disclosed in these two later patents, however, is not completely free from those interferences.

The Young configurations also have additional important limitations, common in other valves commercially supplied for blood-pressure work. First, they have highly objectionable crevices and backwater regions where bubbles can be trapped and resist flushing. Prime among these regions, for instance, is the very long annular space between the new rigid cylinder and the resilient outer tube, in their newer configuration. This space would appear to be very difficult to debubble completely.

Secondly, the Young devices present a "funnel" effect at the entrances to their fine capillary drip-rate bores. Such geometry is extremely susceptible to occlusion of the capillary bore by fluid-borne particles carried in the intravenous liquid. It will be appreciated that even microscopic particles can completely clog a capillary bore that is only a few hundredths of a millimeter in diameter.

Thirdly, some users find it difficult to smoothly control the outer-tube squeeze action used for flush-rate control. This difficulty may be partially a matter of the size of the apparatus relative to the size of the user's hand, or in some cases partially a matter of manual strength or dexterity, but in any event a smoother progressive control of flush-rate fluid flow is desirable.

At the same time, there are commercially available devices that have a snap-back action, for use when flushing is complete, that is more positive than the outer-tube squeeze action in resealing the flush path and thus returning to the drip-rate flow. Some users feel that this more-positive snap-back action is preferable to the other types of return action. It would be ideal if a user could simply choose between smoother progressive control or snap-back action, as preferred at the time of each use.

One device that has a snap-back action is disclosed in Reynolds and Sorenson U.S. Pat. No. 3,675,891. That document may be regarded as the seminal patent in resilient-core valves for blood pressure monitoring systems.

The valve has an elastomeric core in a rigid valve body, and a drip-rate bypass that is embedded in the valve body. Partly because the bypass is associated with the body rather than the core, both the drip and flush flows follow dogleg paths, resulting in some erraticism of debubbling as will be seen, and also some additional cost.

The valve-core opening and closing action is longitudinal with respect to the flush-rate fluid flow—that is to say, the valve core moves bodily parallel to the flush flow, riding on a long cylindrical bellows that lies within the flush channel and is unitary with the core (but functionally distinct). During drip flow, the long bellows is not exposed to the measurement fluid column directly, but only through the seated valve core.

The valve core is conical and engages a conical seat at the downstream end of the bellows. The seating of the core is thus along a thin annular area encircling the center of the conical core. To flush the system, a user pulls outward on a central stem that is attached at the back of the core portion and that extends outward through the long bellows to the exterior of the valve.

Since the core itself is elastomeric and thus resilient, it requires no separate O-ring or like seal to seat hermetically. Further, since the core and bellows are formed as a unitary part, the resilience of the elastomer also provides the necessary biasing action of the cylindrical bellows.

Nevertheless it is noteworthy that, in opening and closing of this valve, the major component of motion is bodily displacement of the entire core portion, as distinguished from resilient deformation to open some part of the valve/seat interface. In this way the underlying operating principle of the Reynolds-Sorenson device is substantially the same as the Cole-Thornton unit.

The core center itself is never restrained but rather extends as a free-floating guide tip into a narrow flush-path outlet chamber. This tip helps the core to reseat reliably when released after flushing.

In the Reynolds-Sorenson configuration both the flush valve and the drip bypass follow dogleg routes, making the likelihood of bubble entrapment strongly dependent upon the orientation of the valve. Debubbling is accordingly tricky.

In particular, bubbles may be too easily trapped below the bellows 28, 31 (as drawn, in Reynolds' FIGS. 2 and 5 respectively), at the bottom right-hand corner of the flush channel 19; or in the top channel 14. During drip flow, bubbles also may be trapped in the flush path outlet chamber 20 and the adjacent lower corner of the cross-connect path 17.

The Reynolds-Sorenson valve is also subject to interfering-resonance problems of the type discussed above. Although in this valve such problems are less severe than in the Young valves, they are nevertheless significant.

In addition, flushing the Reynolds-Sorenson valve requires either considerable dexterity or the use of two hands. Reliable snap-back reseating is provided, but the manual pull-stem does not lend itself to smooth control of flush rate. Finally, because of "funneling" as mentioned above in relation to the Young patents, the Reynolds-Sorenson drip bypass is difficult to keep clear.

It is known among designers of flush-type valves that the relatively low-frequency mechanical resonances found to intrude into the measurement system from some prior-art valves can be understood by analyzing the valve structure, the catheter and other tubing, and the pressure monitor all considered together as a resonant mechanical system. Despite this general understanding, however, prior artisans have failed to reduce such resonances to negligible magnitudes.

Such analysis reveals that relatively low-frequency resonances can arise from a relatively high degree of mechanical compliance or resiliency of some components of a valve unit, as "seen" by the fluid columns in the valve unit and in the fluid-supply lines.

It is well known that in any mechanical system which has a compliant or energy-storing component, resonances are possible at frequencies which vary in an inverse way with the amount of compliance or resiliency. Hence resonance in a relatively low range of frequencies—such as zero to ten or fifteen hertz, the effective frequency range of interest for blood-pressure measurements—can occur if a resilient component or subunit of the valve is too resilient.

It follows that the generation of interfering resonances in this range of interest can be significantly reduced by using less-resilient (i.e., stiffer) materials wherever resilience is required. Interference can be further minimized by reducing the gross size of the resilient or energy-storing element.

That is to say, the magnitude of a resonant vibration can be lowered by decreasing the amount of energy that can be stored in the resilient element. This can be done by reducing the mass of that element.

Still further, the practical effect of a resilient or energy-storing element in a mechanical system can be minimized by lowering the coupling between the resilient element and the rest of the system. That is, if a particular resilient element is present but can neither transfer energy to nor receive energy from the rest of the system efficiently, then the system behaves as if the resilient element were smaller.

These considerations favor valve configurations having very little resilient surface in contact with the pressure-transmitting fluid—or, stated more generally, these principles favor having very little surface that transmits forces between the pressure-transmitting fluid and a resilient element of the system.

Although these principles are known, prior-art valves are subject to objectionable levels of mechanical resonance. Heretofore no valve configuration has been found that makes optimum use of these principles—at least not without compromises that introduce other operating problems.

For example, analyzing the previously discussed Cole and Thornton valve unit, it can be seen that the apparatus is possibly subject to undesirable mechanical resonances because of the mechanical compliance present in the subunit consisting of the valve core, lever and plunger, and a resilient spring that biases the core seal (i.e., the O-ring) against its seat. This composite structure or subunit is directly in contact with the measurement-fluid column, over the face of the valve core—a relatively large surface area (very roughly twenty square millimeters) for transmission of fluid pressure.

Similarly analyzing the Young devices, in the original design the downstream half of the elastomeric outer tubing was in direct contact with the measurement fluid column. This contact extended entirely around the internal circumference of the tube, a much larger surface (very roughly one hundred sixty square millimeters) than in the Cole-Thornton valve; and the elastomeric tubing was loosely in tension, tending to exaggerate or at least not minimize its resiliency.

In the later Young devices, the interposed rigid cylinder reduced the mechanical coupling of the downstream fluid column with the elastomer very greatly, but not entirely—since a narrow annular fluid column remains.

Similarly reviewing the Reynolds-Sorenson unit, it can now be appreciated that the fundamental geometry remains the same as in the Cole-Thornton unit. This is so despite the relatively sophisticated integral design of the valve core, face, seat, biasing bellows and actuator as a single molded elastomeric subunit.

Each unit has a bodily moved core that is exposed across its face area to liquid pressure, and that couples a large compliance to the liquid through that face. In the Reynolds-Sorenson valve this surface (roughly ten or fifteen square millimeters) appears somewhat smaller than that in the Cole-Thornton valve, but remains significant.

In addition another transmission mechanism may operate to couple compliance to the measurement liquid column. This is a second route via the central "core of the core."

By that we mean the central part of the valve core, within the annular seat area, where the elastomeric material is only partially compressed and therefore somewhat resilient and somewhat free to vibrate. A significant surface area of this downstream end of the conical core and of the guide tip is exposed to the measurement fluid in the outlet chamber of the flush valve.

To the extent that vibrations may possibly be transmitted through the core, the long, thin-walled bellows is coupled to the fluid column. Even considered alone the bellows has a sizable resilient surface area and mass.

From this presentation it will be understood that the prior art has not entirely satisfied the need of medical practitioners for an inexpensive flush-valve assembly that has little or no tendency to trap bubbles; that can be used in a smooth progressive-control mode for flushing or in a positive snap-back mode for restoring "drip" operation, as preferred; and that can be made in such a way as to avoid resonances that mask pressure variations.

SUMMARY OF THE DISCLOSURE

Our present invention is particularly effective in meeting all these needs. In fact we have succeeded in providing a configuration that is very easily manufactured, assembled and placed in operation, and yet has all the desirable properties outlined above.

One inventive step that has contributed to our present invention has been the realization that the resonance problem persists in prior-art devices because their geometry does not inherently operate to minimize the coupling of compliance to the liquid in the measurement column.

Another important step has been to realize that the effective compliance of a compliant element can be artificially reduced during sensitive intervals, particularly during blood-pressure measurement, by holding the compliant element squeezed tightly during those intervals. In effect much of the compliance is "used up"; the remaining compliance is a small fraction of the total and may even be negligible.

To make use of this realization, it is necessary to develop a new kind of valve geometry. It is necessary to conceive of a valve configuration in which high compressive stress on the resilient element is permissible, to render the compliance at least partly inoperative.

In such a geometry the needed compliance of the resilient element is allowed to come into operation only at other times—that is, only when the blood-pressure is not being measured.

In the Cole-Thornton and Reynolds-Sorenson devices the resilient elements are compressed, but not very tightly. In both cases a large fraction of the total compliance remains available for interaction with vibrations in the liquid measurement column to cause objectionable resonances.

In both these cases, speaking in general terms, the compression in effect acts longitudinally—that is to say, generally parallel to the liquid flows. Such geometries do not seem readily amenable to squeezing of the resilient elements tightly, although there may be possible configurations in which greater compression could be applied.

Our present invention not only makes use of these realizations, and strategies arising from them in combination with known physical principles, but also makes use of several other innovative features—to virtually eliminate all the previously mentioned adverse characteristics of prior-art valves for blood-pressure monitoring systems. Our invention virtually eliminates resonant effects without at all compromising—and in fact while enhancing—its performance as evaluated by the other criteria outlined above.

Our invention is a flush valve for a blood-pressure measurement catheter. It includes a formed, substantially rigid body, and fluid inlet and outlet paths defined in the body. It also includes a valve-core cavity defined in the body, and a valve seat defined at the floor of the cavity. A resilient valve core is disposed in this cavity, and biased against the valve seat.

The core cooperates with the valve seat in deterring fluid flow between the inlet and outlet paths. At the same time, our invention includes some means for bypassing the seat to communicate between the inlet and outlet paths.

For generality in expression of our invention, we shall refer to these as "drip-rate fluid-flow means." In our invention the drip-rate fluid-flow means are external to the mass of the rigid body—i.e., although within the valve they do not pass within the mass of the body itself.

In addition, our invention has some manually operable means for deforming the resilient valve core to overcome the bias and separate part of the core from the seat—and so to permit flush-rate fluid flow between the inlet and outlet paths. Again for generality, we shall call these the "flush-control means." These concepts of "deforming" the core and separating "part of" it from its seat are as distinguished from translation or bodily motion of the entire core relative to its seat as in the prior-art Cole-Thornton and Reynold-Sorenson valves.

The foregoing may be a definition of our invention in its broadest or most general form. We prefer, however, to incorporate several other features singly or in combination to more fully develop all the advantages of the invention.

In particular, for the necessary resilient material of the valve core we prefer to use material that is no more resilient than necessary—that is to say, relatively stiff material. We also prefer to make the surface area through which fluid at the measurement-column side of the valve core is coupled to resilient material very small.

In our preferred valve, that area is an exposed resilient surface of the resilient core itself. In variant geometries, however (as in prior art), the coupling surface may be an effectively rigid force-transmitting intermediary.

Moreover, we prefer that in a quiescent condition, when the flush-control means are not operated to permit flush-rate fluid flow, the resilient valve core be biased against the seat by the bulk resiliency of the core itself.

We prefer to provide such biasing in a positive engaging action that is transverse to the drip-rate and flush-rate fluid flows—with the valve-core material in compression. (It will accordingly be understood that we prefer to orient the drip-rate fluid flow and the flush-rate fluid flow substantially mutually parallel.)

This biasing, in a positive engaging action transverse to the fluid flows, by placing the core material in compression reduces the effective resilience of the valve core during the quiescent condition.

These preferable features in combination are very useful. Stiffness of the core material and smallness of the coupling surface minimize the coupling of resilient material to fluid, and so minimize the effective compliance which the resilient part of the valve introduces into the monitoring system.

Furthermore, the reduced effective resilience during the quiescent condition raises the resonant frequency of mechanical oscillation of the monitoring system during the quiescent condition—to values substantially outside the range of frequencies of interest in blood-pressure monitoring. As a result, adverse resonant effects on accurate operation of the blood-pressure monitoring system are made substantially insignificant.

We also prefer to provide the drip-rate fluid-flow means in the form of a small-diameter resilient lumen within and through the valve core, communicating between the inlet and outlet paths and bypassing the valve seat. Since this lumen is resilient (though much stiffer than the core) it deforms along with the core proper, and thus offers no interference to flush operation of the valve.

We prefer to provide the lumen as a small-diameter resilient tube, either inserted or molded into the valve core. As will be explained below, however, if preferred it may instead be provided in other forms—for example, in the form of an unsupported lumen formed through the core; or in the form of a molded-in path along the face of the valve seat or the core, or both.

In addition we prefer to provide the core itself as a generally T-shaped resilient member. Part of this member—particularly the "upper" (as in the usual orientation of a letter "T") center of the crossbar of the T—is biased against the seat by the resilience of the member itself.

The extrema of the crossbar are hermetically sealed against the body. In this regard, as will be seen more clearly from the detailed description that follows, the T shaped member actually has a T shape as seen in two different perpendicular cross-sections; in other words, the T is actually a central stem with a three-dimensional flange top, rather than merely a two-dimensional crossbar. Hence by "extrema" we mean not merely the two ends of a two-dimensional crossbar but rather all the peripheral parts of the core surrounding the central stem.

In the preferred configuration now under discussion, the stem of the T shape of the resilient member extends outward from the valve body. The manually operable flush-control means operate by pulling outward on the stem of the T, to deform the resilient T-shaped member and separate the center of the crossbar of the T from the seat.

We prefer to provide outside the valve body a resilient cowling that a user can squeeze to pull the stem outward and initiate flow. This squeeze-controlled cowling provides very easy, sensitive progressive control of flush-rate flows; but tends to prevent inadvertent actuation that might otherwise arise from application of force at just one side of the valve.

The remote end of the stem of the T is accessible outside the valve body. A user can grip that remote end directly, and pull it outward for flush-rate flow. The user can also release the remote end to allow the valve core to "snap back" and thereby achieve the positive reseating of the valve core that some consider desirable.

From the foregoing it can be appreciated that the present invention is a very simple valve in which there are only two (or three, counting the embedded tube) internal working parts, together with a simple external cowling for flush control. No separate 0-ring seals, springs, pins, or the like are required.

All the parts are easily formed by molding in plastic, and easily assembled; hence the cost is very low. Furthermore the configuration is readily amenable to a very nearly in-line fluid path, with elimination of eddy points, niches and other features that could otherwise trap bubbles.

In addition the configuration is amenable to adjustment of resiliencies or compliances to avoid internal resonances in a frequency range that interferes with effective blood-pressure monitoring. More specifically, the system can be made stiff enough that its mechanical resonances are in the range of thirty to forty hertz, well outside the troublesome range of ten to fifteen hertz where blood-pressure variations of interest occur.

The system is also fully amenable to fabrication with a unitary mounting site for a blood-pressure monitoring sensor. Thus the invention provides a single inexpensive disposable unit that performs both pressure sensing and flush control, with all of the advantages just described.

All these operational principles and advantages of the present invention will be more fully appreciated upon consideration of the following detailed description, with reference to the appended drawings, of which:

BRIEF DESCRIPTION OF THE DRAWINGS

FIG. 3 is an exploded perspective view of the same embodiment.

FIG. 4 is an even more enlarged side elevation, mostly in longitudinal section, of the valve core used in the embodiment of FIGS. 1 through 3.

FIG. 5 is an end elevation, at roughly the same scale as FIG. 4, of the same core.

FIG. 6 is a plan view of the same core, partially in horizontal section along line 6—6 of FIG. 5.

FIG. 7 is an elevation, taken in longitudinal section along the line 7—7 in FIG. 2, of the FIG. 1 through 3 embodiment with the flush valve closed.

FIG. 8 is a cross-sectional elevation, taken along the lines 8—8 in FIG. 7, of the same embodiment—also with the flush valve closed.

FIG. 9 is a like view showing the flush valve open.

FIG. 10 is a partial longitudinal section, similar to portions of FIG. 7, but taken along the line 10—10 in FIG. 9 and with the flush valve open.

DETAILED DESCRIPTION OF THE PREFERRED EMBODIMENTS

Figure 1:
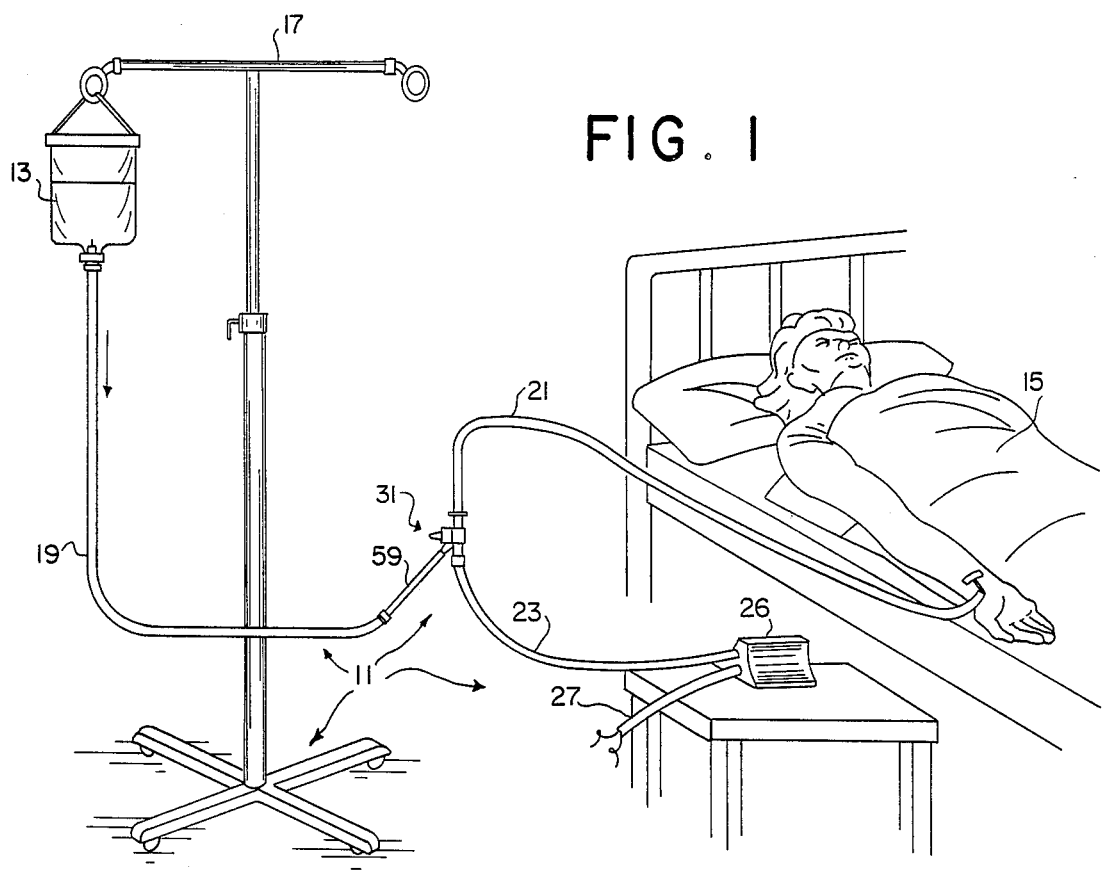
FIG. 1 is a generally schematic view, partially in perspective, showing one preferred embodiment of the invention in use.

As shown in FIG. 1 the valve 31 of our invention is typically used in a system 11 that includes a source container 13 of fluid for intravenous infusion. This intravenous-fluid container 13 is elevated on a suitable rack 17 and usually enclosed in a pressurized bag (not shown) to provide hydraulic head, and connected by a tubulation 19 to an inlet line 59 of our valve 31.

An outlet port 24 of our valve 31 is connected to another tubulation 21, whose interior after preliminary flushing is placed in communication with the bloodstream of a patient 15. Generally this is accomplished by means of a cannula or catheter inserted into the patient's body as shown Another port 34 of the valve 31 is connected by a third tubulation 23 to a pressure-monitoring transducer 26.

Preferably the inlet line 59 and transducer connection 34 are at the underside of the valve 31, so that bubbles tend to move out of both the supply tube 19 and transducer tube 23 into the valve. This arrangement facilitates preliminary flushing of the bubbles out of the system 11.

As is well known, the vent port (not shown) of the transducer 26 is ideally positioned at the same elevation as the middle of the patient's heart. This positioning is intended to avoid a liquid head that would otherwise introduce a spurious pressure differential between the blood pressure in the body and the fluid pressure at the transducer.

FIGS. 2 through 8 show that the valve 31 has a box-like housing 33, with upstanding side walls 39, 41 and end walls 35, 37 all erected upon an upper wall 101, 102 of a through-tube 32-24-34. The valve housing is completed by a separate cover 80, with side tabs 83, 85 and an internal compression block which has an end face 81.

The cover 80 fits onto the housing 33, with the side tabs 83, 85 outside the side walls 39, 41 and the block 81 inserted down into the housing. Except for a central aperture 86, the cover closes the top of the housing 33.

The floor of the housing 33 is a generally flat rectangular surface 42 (see FIGS. 3 and 8), except for relatively narrow recesses 53, 55 formed at the inlet and outlet ends of the housing 33. The recesses 53, 55 are positioned centrally, with respect to the transverse dimension of the valve 31, so that they are aligned above the center of the through-tube 32-24-34 and also are aligned with the center of the inlet tube 59 and inlet fitting 57.

The inlet end of one recess 55 communicates with the inlet fitting 57, and is longitudinally tapered or beveled to form with the inlet fitting 57 a very generally continuous, smoothly contoured passageway. The other recess 53—at the end of the valve that is remote from the inlet fitting 57—communicates with the through-tube 32-24-34 via a port 52 in the housing floor 42.

The recesses 53 and 55, however, are not in mutual communication. They are separated by a raised pedestal 100 that is essentially part of the flat floor 42 of the housing. Upon this floor 42, particularly including the pedestal 100, rests a central part of the bottom surface 63 (FIGS. 4 and 5) of the valve core 60.

The recesses 53, 55 thus form flush-rate flow channels in the floor 42 of the valve housing 33. In the quiescent condition of the valve, when the valve is able to pass only drip-rate flows, the flush-rate flow channel recesses 53, 55 are effectively blocked by the pedestal 100 in cooperation with the bottom surface 63 of the core 60.

(The recesses are, however, beveled or tapered upward to the top of the pedestal 100 for purposes to be explained shortly.)

The core 60 consists of a shallow, generally rectangular base 65 with end planes 67, 69 and side planes 71, 73; and a slender stem 62 of square cross-section that is extended into a contoured elongate hilt or handle 61 with grip-enhancing cleats 71 and a circumferential flange 72.

The circular central area of the core base 65 immediately surrounding the stem 62 is recessed, so that the peripheral parts of the base 65 form a shallow flat-topped wall 70. This wall is rectangular at its outer vertical surfaces 67, 69, 71, 73; but is circular at its inner vertical surface 70.

When the valve is assembled, the base 65 of the valve core 60 rests on the housing floor 42 and the valve-core stem 62 and handle 61 protrude upward through the aperture 86 in the housing cover 80. Meanwhile the top of the peripheral wall 70 is firmly engaged and held down by the peripheral block 81, 80′ (FIGS. 2, 3, and 7 through 10) formed in the undersurface of the cover 80. The block 81, 80′ is permanently press-fitted into the housing 33.

By virtue of the pressure against the top of the peripheral wall 70, the base 65 of the valve core 60 not only firmly engages its "seat"—which consists of the housing floor 42 and in particular the central pedestal 100 between the recesses 53 and 55—but also the valve core 60 or more particularly its base 65 is compressed. The compressive stress in the base 65 after valve assembly is roughly $14 \times 10^6$ dyne per square centimeter.

Whereas the elasticity of the valve-core material when in a free condition is approximately $7 \times 10^{10}$ dynes/cm$^2$, its elasticity when thus compressed in the assembled housing is $18\ 35 \times 10^{10}$ dynes/cm$^2$.

Beveled flow recesses are also formed in the underside of the core 60. More specifically, the end faces 67, 69 and adjacent bottom surface 63 (FIGS. 3 through 7) of the valve core 60 are beveled away or recessed upward—along the centerline of the valve, as with the recesses 53, 55 in the housing floor 42.

Hence the beveled or upwardly recessed surfaces 68, 66 at the inlet and outlet ends of the core 60 are aligned immediately above, respectively, the beveled entryway to the inlet recess 55 and the exit port 52 that terminates the outlet recess 53. The recesses cut away in the ends of the core 60 thus cooperate with the previously discussed recesses in the valve-housing floor 42, and with the inlet fitting 57 and outlet port 52, to form relatively smooth and continuous conduits for flush-rate flow.

It will be appreciated that the drawings are much larger than the actual parts. Accordingly, minor irregularities in the flow paths as seen in the illustrations are nearly microscopic in actuality.

A very fine plastic capillary 78 is positioned within the valve core 60, just above the bottom surface 63 of the core. This capillary 78 is oriented longitudinally, and is just long enough to span the length of the valve core 60 between the bottom recesses or beveled-away portions 66, 68 of the core.

In particular the inlet end 77 (FIGS. 4, 7, 10 and particularly 12) of the capillary protrudes slightly from the inlet end of the core 60. This protrusion prevents funneling of microscopic debris into the capillary and so tends to prevent clogging.

With this geometry, the likelihood of such debris entering the capillary is determined primarily by the ratio of the capillary-bore cross-sectional area to the surface area formed at the blind "end of the tunnel" 55, 56, 63. The capillary bore is only on the order of a twentieth to a tenth of a millimeter, making the cross-section on the order of two to eight thousandths of a square millimeter. The fraction of the total surface area that is represented by this capillary cross-section is extremely tiny.

Nevertheless this small capillary bore does conduct enough liquid to define the drip-rate fluid flow desired. Made of the material known in industry as "TFE," the capillary is about eight millimeters long. At this length, and under the pressures prevailing in normal use of our invention, a capillary of diameter just under one-twentieth millimeter conducts on the order of three cubic centimeters of normal saline per hour; while a capillary of diameter one-tenth millimeter conducts on the order of thirty cubic centimeters per hour.

We have found that tubes of this small diameter do not conduct according to classical relationships. Rather, in extremely approximate terms, the flow rate is proportional to the cube of the bore diameter and inversely proportional to the bore length.

The first part of this relation may be stated more generally: flow rate is very approximately proportional to the cross-sectional area raised to the power three-halves (i.e., one and a half). Thus for a passageway of roughly rectangular cross-section (sharp corners being virtually impossible to achieve in these small devices), the flow rate is very approximately proportional to the product of length and width, all raised to the power three-halves.

For several reasons it is necessary to discuss the flow and dimension relationships of this device in terms of extreme approximation or in terms of orders of magnitude, rather than in precise terms. For example, in a bore whose nominal diameter is one-twentieth millimeter, a minuscule deviation in bore diameter of only one-hundredth millimeter represents an error of twenty percent in diameter—and roughly seventy percent in flow rate.

Furthermore, normal temperature variations in the intravenous fluid can change the flow rate by a factor of two. The flow rate is proportional to the effective hydraulic head, which depends upon elevation of the meniscus of fluid in the supply bottle, pressurization (if any) of the bottle, elevation of the patient's body and thus the measurement point in the patient's bloodstream, and back-pressure (nominally one hundred millimeters of mercury from the patient's blood-pumping mechanism.

Medical personnel are instructed to establish a hydraulic head of three hundred millimeters of mercury by proper positioning of the supply bottle relative to the patient's body, but neither this adjustment nor operation of any pressurizing device is likely to be highly precise. Likewise, back-pressure from the patient is subject to great variation on account of the patient's general condition, state of anesthesia and other medication, etc.

For all these reasons, it will be appreciated that the relationships stated here between flow rate, length and transverse dimensions are never observed under ideal conditions and are necessarily approximations. Assuming the ideal net head of two hundred millimeters of mercury, and assuming the correct nominal temperature of the intravenous liquid, the flow rate in the system is roughly:

$$F = 300,000 \times \frac{(W \times D)^{3/2}}{L} \text{ cubic centimeters per hour,}$$

where W, D and L are respectively the width, depth and length of the capillary bore in millimeters.

The general structure and operation of the valve relating to its quiescent condition, for metering the drip-rate flow, have now been described completely. It remains only to complete the presentation of structural features and operation related to flush-rate flow.

As shown in FIGS. 2, 3 and 7 through 10 the valve-core hilt or handle 63 protrudes through an aperture 86 in the housing cover 80—and then through another aperture 90 in a cowling 91 that encircles the upper (as drawn) half or two thirds of the valve housing 33. The ends 93, 95 of the cowling 91 curl down around the respective sides 39, 41 of the housing 33.

Figure 2:
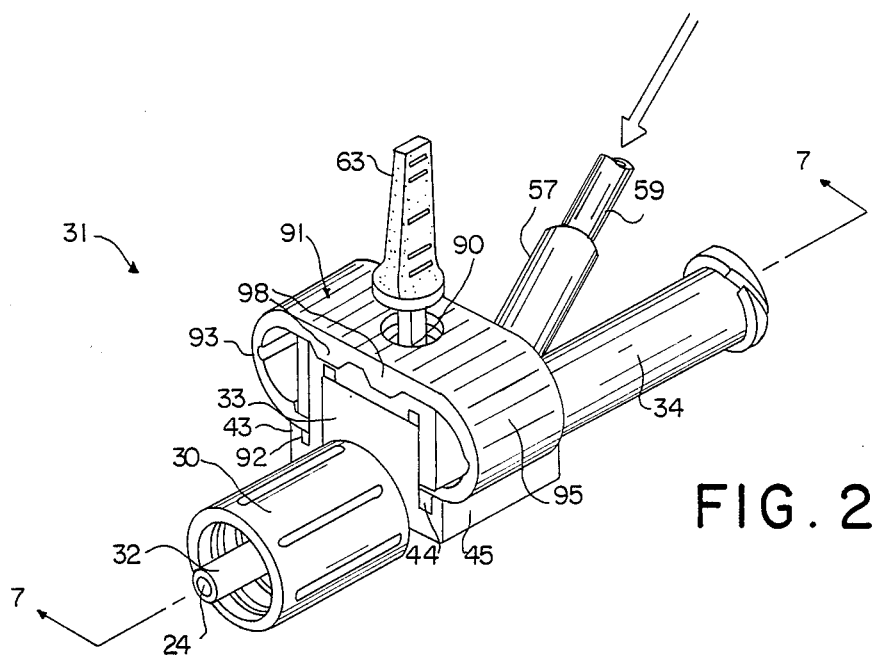
FIG. 2 is an enlarged perspective view of the FIG. 1 embodiment.

The cowling ends 93, 95 terminate in respective retaining flanges 92, 94. As best seen in FIGS. 2 and 8, these flanges are captured in narrow retaining slots 47, 49 formed near the bottom of the housing side walls 39, 41. The slots 47, 49 are defined by upstanding shallow rails 43, 45 spaced slightly away from the bottom edges of the respective walls 39, 41.

The cowling flanges 92, 94 are captured in these retaining slots 47, 49 by the respective side tabs 83, 85 of the housing cover 80. The tabs 83, 85 extend downward along the outside of the side walls 39, 41 to a level just above the rails 43, 45—with just enough clearance for passage of the cowling ends.

To produce flush-rate flow through the valve, a user applies finger pressure as illustrated in FIG. 9 to both wings or limbs 93, 95 of the cowling 91. While the retaining flanges 92, 94 remain captured in the side slots 47, 49 as just described, the cowling is sufficiently stiff that it cannot simply collapse inward but rather deforms upward at its center.

To help constrain the cowling to this mode of deformation, it is formed with relatively thick stiffening reinforcement regions 89, in the areas where it is to remain stiff enough to push outward on the stem flange 72. It also has reduced-thickness portions 93, 95 in the areas where it is to bend.

In this deformation the cowling carries upward with it the circumferential flange 72 formed partway up the valve stem 62-72-61. To assist in this function, two lateral shelves 99 (FIGS. 3 and 8) are formed inside the bottom half of the cowling aperture 90.

The bottom of the circumferential flange 72 on the valve stem rests within the cowling aperture 90. As shown in FIG. 9, however, the stem flange 72 tends to be elevated by the shelves 99 when the cowling is laterally squeezed.

(For assembly purposes, on the other hand, the stem flange 72 is readily pulled through the narrow part of the aperture 90 between the shelves 99. In this maneuver one simply makes use of the resiliency of the materials of both components to deform both enough to permit passage.)

If preferred, instead of squeezing the cowling to initiate flush-rate flow a user can grasp the stem handle 61 directly and pull it outward. The only drawback to this procedure is that the user either must use both hands— one to pull the handle 61, and the other to hold the valve housing 33 or associated tubing 32, 34, etc.—or must apply considerable manual dexterity to perform both these functions with one hand.

When the user by either method pulls the remote end of the stem 62-72-61 outward, the narrow inner segment 62 of the stem pulls outward on the central part of the valve core. Then as shown in FIGS. 9 and 10 the central part of the core undersurface 63 deforms or bows away from the housing floor or seat 42, and particularly away from the central pedestal 57 that separates the recesses 53, 55 in the seat 42.

The desirability of beveling the inner ends of both seat recesses 53, 55 can now be seen in FIG. 10. As shown, the inboard bevel surfaces cooperate with the bowed undersurface 63 of the core 60 to form a temporary but relatively continuous, smooth flush-rate passageway. This passageway extends from the inlet fitting 57 into the outlet aperture 52 that communicates with the through-tube bore 24.

FIG. 10 also shows how the capillary tube 78 deforms with the valve-core base 60. The capillary is considerably stiffer than the core, and so retains its structural integrity in this deformation; but it is resilient enough to permit the valve-core base 60 to undergo the necessary deformation to open the flush-rate pathway as shown in the drawing.

Purely for shorthand descriptive purposes we point out that the resilient valve core 60 has the shape of an inverted letter "T", as drawn, and that it has this shape when viewed in section regardless of the section taken. We also note that the crossbar of the T (i.e. the base 65 of the core) seats in the housing—specifically in what would be the "top" of the housing, if the T were right-side-up.

There the extrema of the crossbar are clamped under compression against the seat, by the peripheral block 80' formed in the inside of the housing cover 80. We use the word "extrema" rather than "ends" to emphasize that the core 60 has a T shape as viewed in any section, so that the crossbar is really not just a two-dimensional line but a three-dimensional flange. The extrema are thus the entire periphery of that rectangular flange.

Continuing this shorthand description, portions of the "upper" side (considering the T to be right-side-up) of the extrema are relieved to help form a smooth fluid-flow transition with the inlet and outlet paths. Further, it is the stem of the T that is pulled outward to initiate flush flow by separating the center of the T crossbar from the seat.

As will now be clear, the valve is readily operable by gripping and pulling the stem of the T directly, or by squeezing the cowling to pull the stem outward indirectly. In addition, remotely or even automatically actuated equipment such as a solenoid is readily interposed to pull the stem outward. A solenoid or other actuator can be controlled by a pushbutton located elsewhere, or energized in an automatic-control sequence by the electronics associated, for example, with the pressure-monitoring system.

Figure 11:
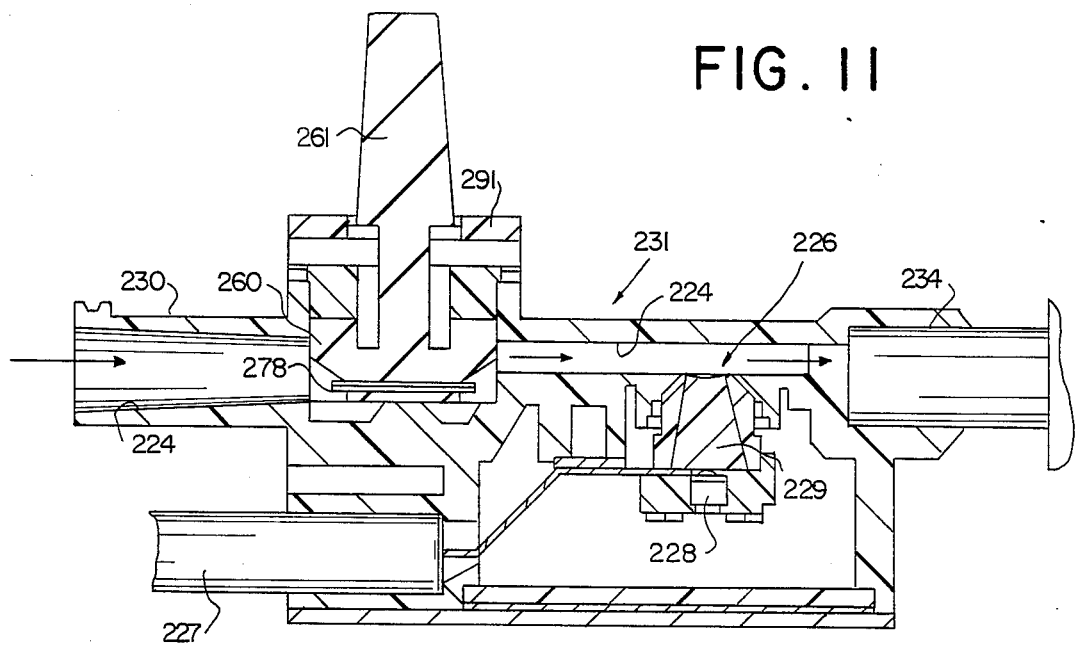
FIG. 11 is a longitudinal section of a preferred embodiment of the invention having integral mounting for a pressure transducer, and also showing the transducer mounted and connected.
Figure 12:
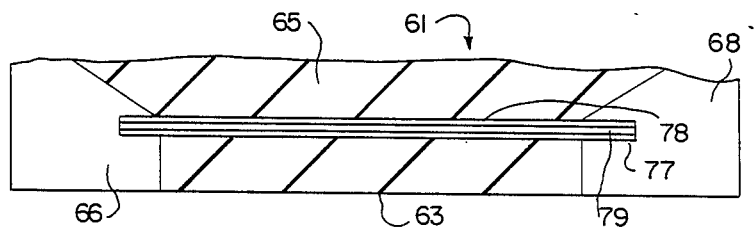
FIG. 12 is a very greatly enlarged elevation, in longitudinal section, of the portion of FIG. 4 enclosed by line 12—12—showing the drip-rate flow-restricting tube in the core.

We consider it particularly advantageous to incorporate a pressure-sensor into a single assembly with our flush valve. FIG. 11 shows such a unitary assembly. All the parts that correspond to those shown in previous drawings, already discussed, appear in FIG. 11 with reference numerals that are the same as in the previous drawings—except for addition of a prefix "2." Thus the valve core is here 260, etc.

At the downstream or "patient" end of the structure there is now mounted a state-of-the-art pressure transducer subassembly 226. This subassembly may preferably include a diaphragm and reference pressure chamber 228, an isolating gel 229 or like, and electrical connections as at 227.

Outside the outlet fitting 234, a venting stopcock (not illustrated) is advantageously mounted for use in debubbling. Such a stopcock may, for example, connect the valve and pressure-transducer assembly to a vent port to allow escape of bubbles, without venting the line that is attached to the patient.

Figure 13:
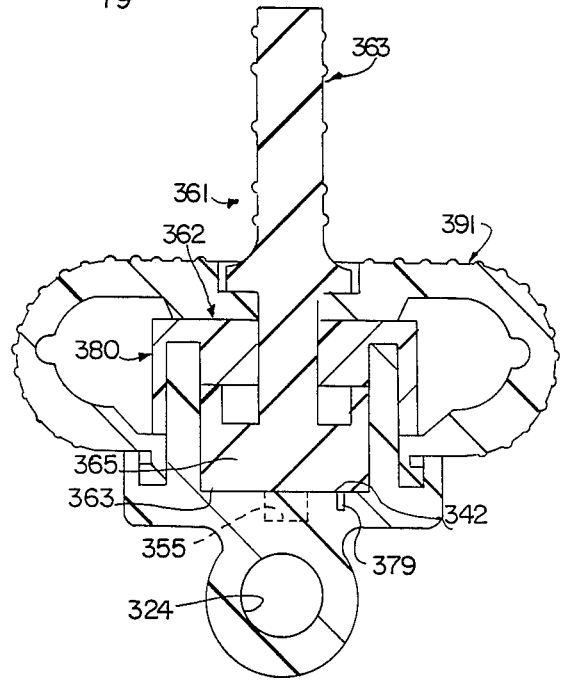
FIG. 13 is a cross-sectional elevation, similar to FIG. 8, of a variant form of the FIG. 1 through 10 embodiment in which the flow-restrictor tube is replaced by a groove in the valve seat.
Figure 14:
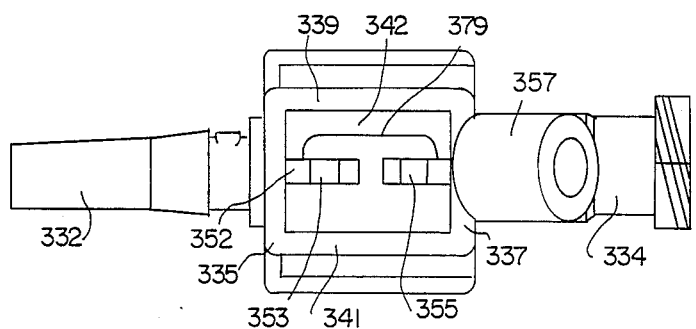
FIG. 14 is a plan view of the valve seat in the FIG. 13 embodiment, showing the groove following a relatively direct route.
Figure 15:
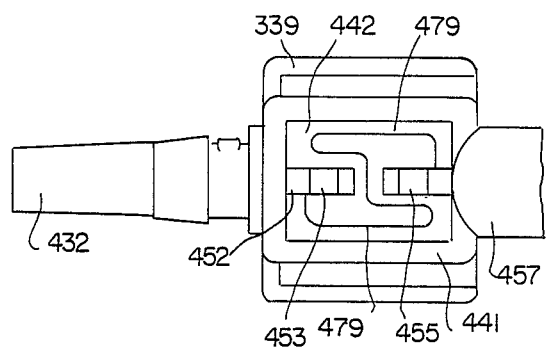
FIG. 15 is a like plan view of a valve seat in a variant form of the FIG. 13 and 14 embodiment. In this form the groove follows a relatively indirect route.

It is possible to dispense with the additional step of mounting a capillary 78 through the valve core 60. As shown in FIGS. 13 through 15, this can be done by instead forming a drip-rate flow controlling passage 379 in the form of a groove in the face of the valve seat 342.

In principle the groove can be formed instead in the mating surface of the valve core—or even partly in the seat and partly in the core. We prefer, however, to form it only in the seat.

As previously mentioned, the drip-rate flow is extremely sensitive to even minute variations in the dimensions of the flow-restrictor passage. If the groove were in the valve core, the resilience of the core material would make it very difficult to avoid significant variation of groove dimensions and even shape.

Even if the groove is formed in the seat, uncontrolled variation of its effective depth can be a problem, since the free end of the groove is closed by the mating surface of the compressed resilient valve core. That surface tends to bulge or intrude into the groove—very little in absolute terms, but potentially enough to cause a very significant loss of depth in fractional or relative terms. Even the variation in the amount of such inward bulge (with changing temperature, fluid pressure, elastomer batch properties or other operating parameters, as well as molding tolerances) is likely to be significant.

For example, if as illustrated in FIG. 14 a groove 379 follows a relatively direct path—a path that is roughly eight to ten millimeters long—and if the groove is one-twentieth millimeter wide, the groove 379 should be about one-twenty-fifth millimeter deep for a drip-rate flow of three cubic centimeters per hour. Using the relationships introduced earlier, a variation in bulge-created depth loss of only one-hundredth millimeter amounts to a twenty-five-percent variation in depth and area, or a forty-percent variation in flow rate. A depth variation of two-hundredths millimeter comes to eighty-four percent in flow rate.

For a drip-rate flow of thirty cubic centimeters per hour, however, such a groove should be about one-eighth millimeter deep; and even a variation of two-hundredths millimeter represents only about twenty-three percent in flow rate. As suggested by these examples, even a somewhat direct groove path such as that in FIG. 14 may be practical for relatively high desired drip rates.

Practicality for both flow rates, however, can be enhanced by making use of a groove 479 with a highly elongated, indirect groove path such as that in FIG. 15. Since this path is somewhat more than three and a half times as long as that in FIG. 14, the same flow-restricting properties can be obtained with a groove that is the same width but deeper by the factor three and a half taken to the root three-halves (i.e., to the power two-thirds).

In other words, the groove can be more than twice as deep. The three-cubic-centimeter-per-hour groove can now be about one-twelfth millimeter deep, and the thirty-cubic-centimeter-per-hour groove can be nearly one-third millimeter deep. For these grooves, a variation of two-hundredths millimeter represents respectively forty and nine percent in flow rate. For an even longer path—for example, twice again as long as that in FIG. 15—a variation of two-hundredths millimeter can be reduced, for the two rates under discussion respectively, to twenty-one percent and six percent in flow rate.

Based on extensive experimentation and trial-and-error refinement of our invention, as well as calculations, we have come to the conclusion that it is preferable to make the groove at least twice as deep as it is wide. This may be regarded as a good practical criterion for use in optimizing our invention, in the types of applications for which it is intended.

Approximate dimensions in millimeters (generally to the nearest millimeter) of some other elements of the preferred embodiments of our invention are:

| | |
|---|---|
| length of the valve-core base | 10 |
| length of the flat central pad at the centerline of the base | 6 |
| width of the valve-core base | 7 |
| uncompressed height of the valve-core base | 4.3 |
| compressed height of the valve-core base | 4.1 |
| width of the beveled channels in the valve-core base | 2 |
| height of the beveled channels in the valve-core base | 2.5 |
| width of the beveled recesses in the valve seat | 1.5 |
| depth of the beveled recesses in the valve seat | 7 |
| length of the beveled recesses in the valve seat | 4 |

From the dimensions relating to the beveled channels in the valve-core base it can be calculated that the outlet-channel surface area exposed to the measurement liquid column is roughly fourteen square millimeters. This value is comparable to the exposed core area in the Reynold-Sorenson unit—but here the valve geometry allows for higher compression of the entire core.

Of this total area, the part of the core volume that is exposed through the six-square-millimeter inclined "roof" wall is under moderate compression. The part that is exposed through the beveled channel side walls is under somewhat greater compression.

The core material is preferably medical-grade silicone rubber, durometer Shore A fifty-five to sixty—which is a moderately stiff material at the outset. After compression by about thirteen percent under the housing-cover block 80′, the effective durometer of this material is roughly 20 Shore units higher.

Core elasticities, in terms of "volume expansion of the system" or volume change per unit applied pressure, are on the order of 0.5 cubic millimeters per hundred millimeters of mercury for the uncompressed core; and a calculated 0.08 cubic millimeters per hundred millimeters of mercury for the compressed core.

Compressive stress in the core is on the order of $14 \times 10^6$ dyne per square centimeter. The resonant frequencies of the overall system are raised to thirty hertz and higher.

It will be understood that the foregoing disclosure is intended to be merely exemplary, and not to limit the scope of the invention—which is to be determined by reference to the appended claims.

We claim:

1. A flush valve for a blood-pressure monitoring system, comprising:
   a formed substantially rigid body;
   fluid inlet and outlet paths defined in the body;
   a valve-core cavity defined in the body, said cavity having an interior and a floor;
   a valve seat defined at the floor of the cavity;
   a valve core of a resilient material disposed in the cavity and biased against the valve seat to cooperate with the valve seat in substantially preventing flush-rate fluid flow between the inlet and outlet paths;
   drip-rate fluid-flow means comprising a small-diameter lumen passing through said valve core of resilient material bypassing the valve seat to communicate between the inlet and outlet paths to permit drip-rate fluid flow between the inlet and outlet paths; and
   operable flush-control means for deforming the resilient valve core to overcome the bias and separate part of the core from the seat, to permit flush-rate fluid flow between the inlet and outlet paths.

2. The valve of claim 1, for use with such a blood-pressure monitoring system that monitors pressure in fluid at one side of the valve core, primarily during a quiescent condition when the flush-control means are not operated to permit flush-rate fluid flow; and wherein:
   the drip-rate fluid flow and flush-rate fluid flow are mutually substantially parallel;
   the surface area through which fluid at said one side of the valve core is adapted to be coupled to the resilient material of the valve core is small;
   in such quiescent condition when the flush-control means are not operated to permit flush-rate fluid flow, the resilient valve core is biased against the seat by the resiliency of the core itself, in a positive engaging action that is transverse to the drip-rate and flush-rate fluid flows, with the valve-core material in compression;
   said biasing in a positive engaging action transverse to the fluid flows, with the valve-core material in compression, reduces the effective resilience of the valve core during such quiescent condition;
   whereby the smallness of the fluid coupled surface area minimizes the mechanical oscillatory coupling of the resilient material to fluid;
   whereby the smallness of the fluid coupled surface area and the reduced effective resilience during such quiescent condition, together minimize the compliance of the monitoring system as a resonant system and thereby raise the frequency of mechanical oscillation of the monitoring system during such quiescent condition substantially outside the range of frequencies of interest in such blood-pressure monitoring; and
   whereby adverse resonant effects on accurate operation of such blood-pressure monitoring system are made substantially insignificant.

3. The valve of claim 2, wherein:
   the surface area through which fluid at said one side of the valve core is adapted to be coupled to the resilient material of the valve core is less than fifteen square millimeters.

4. The valve of claim 2, wherein:
   the surface area through which fluid at said one side of the valve core is adapted to be coupled to the resilient material of the valve core is a resilient surface of the core itself that is adapted to be exposed to the fluid.

5. The valve of claim 2, wherein:
   the compression of the valve core produces compliance in the monitoring system on the order of 0.08 cubic millimeters per hundred millimeters of mercury;
   the elasticity of the valve core when uncompressed is on the order of $7 \times 10^{10}$ dynes/cm$^2$;
   the effective elasticity of the valve core when in compression during said quiescent condition is on the order of $14 \times 10^6$ dynes/cm$^2$; and
   resonant frequencies of the monitoring system are raised to thirty hertz and higher.

6. The flush valve of claim 2, wherein said small-diameter lumen is oriented substantially perpendicular to the direction of said bias between said valve core and said valve seat, and communicating between the inlet and outlet paths and bypassing the valve seat.

7. The flush valve of claim 2, wherein:
   said small diameter lumen comprises: a small-diameter tube disposed within and through the valve core and oriented substantially perpendicular to the direction of said bias between said valve core and said valve seat, and communicating between the inlet and outlet paths and bypassing the valve seat;
   the tube has an end that protrudes out from the valve core into the inlet path;
   thereby minimizing occlusion of the tube by particles funneled into the tube along the inlet path and valve core; and
   the tube is sufficiently resilient to deform away from the valve seat with the valve core, when the operable means are operated to permit flush-rate fluid flow; but is sufficiently rigid in comparison with the valve-core material to remain open when the valve-core material is in compression.

8. The flush valve of claim 7, wherein:
   the tube has an internal diameter on the order of one-twentieth millimeter; and
   the drip-rate fluid flow is on the order of three cubic centimeters per hour.

9. The flush valve of claim 7, wherein:
   the tube has an internal diameter on the order of one-tenth millimeter; and
   the drip-rate fluid flow is on the order of thirty cubic centimeters per hour.

10. The flush valve of claim 1, wherein: said small diameter lumen comprises a small-diameter resilient tube disposed within and through the valve core and oriented substantially perpendicular to the direction of said bias between said valve core and said valve seat, and communicating between the inlet and outlet paths and bypassing the valve seat; and the resilient tube has an end that protrudes out from the valve core into the inlet path;

thereby minimizing occlusion of the tube by debris funneled into the tube along the inlet path and valve core.

11. The flush valve of claim 10, wherein:

the tube has an internal diameter on the order of one-twentieth millimeter; and the drip-rate fluid flow is on the order of three cubic centimeters per hour.

12. The flush valve of claim 10, wherein:

the tube has an internal diameter on the order of one-tenth millimeter or less; and the drip-rate fluid flow is on the order of thirty cubic centimeters per hour.

13. The flush valve of claim 1, further comprising:

at least one fluid flow channel formed as a distinct recess in and along a surface of the cavity and communicating with the fluid inlet or outlet path; and wherein the valve seat is disposed to block the channel;

wherein the valve core in cooperating with the valve seat substantially prevents flush-rate fluid flow between the inlet and outlet paths along the channel; and wherein the operable flush-control means permit flush-rate fluid flow between the inlet and outlet paths along the channel.

14. The flush valve of claim 1, wherein:

the core comprises a generally T-shaped resilient member; said T-shaped resilient member comprising a staff and a cross bar forming said T-shape, said cross bar having an upper surface and two extrema, the upper surface of the crossbar of the T shape of the resilient member is biased against the seat by the resilience of the member;

the extrema of the crossbar of the T shape of the resilient member are hermetically sealed against the body;

the staff of the T shape of the resilient member extends outward from the body; and the operable flush-control means operate by pulling outward on the staff of the T shape of the resilient member to deform the resilient member and separate the crossbar of the T shape from the seat.

15. The flush valve of claim 14, wherein:

the T-shaped resilient member is a unitary formed member.

16. The flush valve of claim 15, wherein:

the small diameter lumen comprises a small-diameter resilient tube disposed within and through the T-shaped resilient member, communicating between the inlet and outlet paths and bypassing the valve seat.

17. The flush valve of claim 16, wherein:

the T-shaped resilient member is molded around the small-diameter resilient tube.

18. The flush valve of claim 14, wherein:

portions of the upper surface of the extrema of the crossbar of the T shape of the resilient member that are aligned with the inlet and outlet paths respectively are relieved to cooperate with the interior of the valve-core cavity to form a smooth fluid-flow transition with the inlet and outlet paths.

19. The flush valve of claim 18, wherein:

the inlet and outlet paths, the relieved portions of the crossbar of the resilient member, and the interior of the valve-core cavity are all defined by smooth, gently tapering, well-fitted surfaces forming a substantially in-line flush path, substantially without crevices or eddy points that might trap gas bubbles and prevent their being flushed out of the valve.

20. The flush valve of claim 1, wherein the operable flush-control means comprise:

a generally extensile member secured to or integral with a back side of the valve core, and extending therefrom outward from the body; and manually manipulable means disposed substantially outside the body for drawing the extensile member outward with respect to the body to deform the core and effect flushing.

21. The flush valve of claim 20, wherein:

the manually manipulable means comprises a resilient cowling that is secured to exterior sides of the body, and that engages the extensile member outside the body, and that is adapted to be manually squeezed between two fingers to force the extensile member outward from the body, to deform the core and effect flushing;

whereby the manually manipulable means resists inadvertent actuation by pressure applied at only one side of the valve.

22. The flush valve of claim 20, wherein:

the extensile member is also directly accessible outside the body to be manually directly grasped and pulled outward to deform the core and effect flushing;

whereby a user of the valve can select between manipulating said manually manipulable means and direct grasping and pulling of the extensile member, to effect flushing.

23. The flush valve of claim 1, further comprising:

an electromechanical pressure transducer mounted in the body and exposed to fluid pressure within the outlet path, for generating electrical signals used in measurement of such blood pressure adapted to be transmitted through fluid in the valve; and electrical connections from the transducer for connection to electronic apparatus for utilization of the signals and determination of such blood pressure.

24. The flush valve of claim 1, further comprising:

an electromechanical pressure transducer mounted in the body and exposed to fluid pressure within the outlet path, for generating electrical signals used in measurement of such blood pressure adapted to be transmitted through fluid in the valve; and electrical connections from the transducer for connection to electronic apparatus for utilization of the signals and determination of such blood pressure;

said electronic apparatus being operated to monitor blood pressure primarily during a quiescent condition when the flush-control means are not operated to permit flush-rate fluid flow;

wherein the drip-rate fluid flow and flush-rate fluid flow are mutually substantially parallel;

wherein the resilient surface of the valve core that is exposed to fluid is much smaller than the rigid surface of the body that is exposed to fluid;

wherein in such quiescent condition when the flush-control means are not operated to permit flush-rate fluid flow, the resilient valve core is biased against the seat by the resiliency of the core itself, in a positive engaging action that is transverse to the drip-rate and flush-rate fluid flows, with the valve-core material in compression;

wherein said biasing in a positive engaging action transverse to the fluid flows, with the valve-core material in compression, reduces the effective resilience of the valve core during such quiescent condition;

whereby adverse resonant effects on accurate operation of such blood-pressure monitoring system are made substantially insignificant.

25. The flush valve of claim 1, wherein:
the operable means are manually operable.

26. A flush valve for a blood-pressure monitoring system, comprising:
a formed substantially rigid body;
fluid inlet and outlet paths defined in the body;
a valve-core cavity defined in the body and having an interior;
at least one fluid flow channel defined along one side of the cavity and communicating with the fluid inlet or outlet path;
a valve seat defined at the same side of the cavity and disposed to block the channel;
a valve core of a resilient material disposed in the cavity and biased against the valve seat to cooperate with the valve seat in substantially preventing flush-rate fluid flow between the inlet and outlet paths along the channel, and wherein:
the core comprises a generally T-shaped resilient member, said T-shaped resilient member comprising a staff and a cross bar forming said T-shape, said cross bar having an upper surface and two extrema;
the upper surface of the crossbar of the T shape of the resilient member is biased against the seat by the resilience of the member,
the extrema of the crossbar of the T shape of the resilient member are hermetically sealed against the body,
the staff of the T shape of the resilient member extends outward from the body;
a small-diameter resilient tube disposed within and through the valve core and bypassing the valve seat to communicate between the inlet and outlet paths; and
manually manipulable means disposed substantially outside the body for drawing the staff of the T shape of the resilient member outward with respect to the body to deform the resilient valve core overcoming the bias and separate the core from the seat, to effect flush-rate fluid flow along the channel between the inlet and outlet paths; and wherein portions of the extrema of the crossbar of the T shape of the resilient member that are aligned with the inlet and outlet paths respectively are relieved to cooperate with the channel to form a smooth fluid-flow transition with the inlet and outlet paths; and wherein the inlet and outlet paths, the relieved portions of the crossbar of the resilient member, and the interior of the valve-core cavity are all defined by smooth, gently tapering, well-fitted surfaces forming a substantially in-line flush path, substantially without crevices or eddy points that might trap gas bubbles.

27. The flush valve of claim 26, wherein:
the T-shaped resilient member is a unitary formed member.

28. The flush valve of claim 26, wherein:
the manually manipulable means comprises a resilient cowling that is secured to exterior sides of the body, and that engages the staff of the T shape of the resilient member outside the body, and that is adapted to be manually squeezed between two fingers to force the staff outward from the body, to deform the core and effect flushing;
whereby the manually manipulable means resists inadvertent actuation by pressure applied at only one side of the valve.

29. The flush valve of claim 28, wherein:
the staff of the T is also directly accessible outside the body to be manually directly grasped and pulled outward to deform the core and effect flushing;
whereby, to effect flushing, a user of the valve can select between (1) manipulating the manually manipulable means and (2) direct grasping and pulling of the staff of the T.

30. The flush valve of claim 26, further comprising:
an electromechanical pressure transducer mounted in the body and exposed to fluid pressure within the outlet path, for generating electrical signals used in measurement of such blood pressure adapted to be transmitted through fluid in the valve; and
electrical connections from the transducer for connection to electronic apparatus for utilization of the signals and determination of such blood pressure.

* * * * *